US00PP32864P2

(12) United States Plant Patent
Baars

(10) Patent No.: US PP32,864 P2
(45) Date of Patent: Mar. 2, 2021

(54) MUSHROOM PLANT NAMED 'ALLERPO'

(50) Latin Name: *Pleurotus ostreatus*
Varietal Denomination: ALLERPRO

(71) Applicant: Stichting Wageningen Research—Wageningen Plant Research, Wageningen (NL)

(72) Inventor: Johannes Jacobus Petrus Baars, Maasbree (NL)

(73) Assignee: Stichting Wageningen Research—Wageningen Plant Research, Wageningen (NL)

( * ) Notice: Subject to any disclaimer, the term of this patent is extended or adjusted under 35 U.S.C. 154(b) by 0 days.

(21) Appl. No.: 16/602,521

(22) Filed: Oct. 22, 2019

(51) Int. Cl.
*A01H 5/00* (2018.01)

(52) U.S. Cl.
USPC ..... Plt./394

(58) Field of Classification Search
USPC ..... Plt./394
CPC ..... A01H 5/00
See application file for complete search history.

(56) References Cited

PUBLICATIONS

PLUTO Plant Variety Database May 9, 2020.p. 1.*

* cited by examiner

*Primary Examiner* — Annette H Para
(74) *Attorney, Agent, or Firm* — The Webb Law Firm

(57) ABSTRACT

'ALLERPO' is a new variety of oyster mushroom that produces no spores and has brown colored caps.

6 Drawing Sheets

Botanical classification: *Pleurotus ostreatus*.
Varietal denomination: 'ALLERPO'.

BACKGROUND OF THE INVENTION

The present invention comprises a new and distinct cultivar of mushroom of the species *Pleurotus ostreatus* known by the varietal name 'ALLERPO'. The new variety was discovered in Wageningen, The Netherlands in January of 2004 as part of a planned breeding program. The purpose of the breeding program was to develop a sporeless strain of oyster mushroom. 'ALLERPO' was first asexually reproduced in March of 2004 at the same location by maintaining vegetative mycelium on agar slants and in the vapor phase of liquid nitrogen. The new variety has been trial and field tested and has been found to retain its distinctive characteristics and remain true to type through successive propagations.

DESCRIPTION OF THE DRAWINGS

The accompanying photographic drawings illustrate the new variety, with the color being as nearly true as is possible with color illustrations of this type.

DETAILED DESCRIPTION OF THE INVENTION

Figure 1:
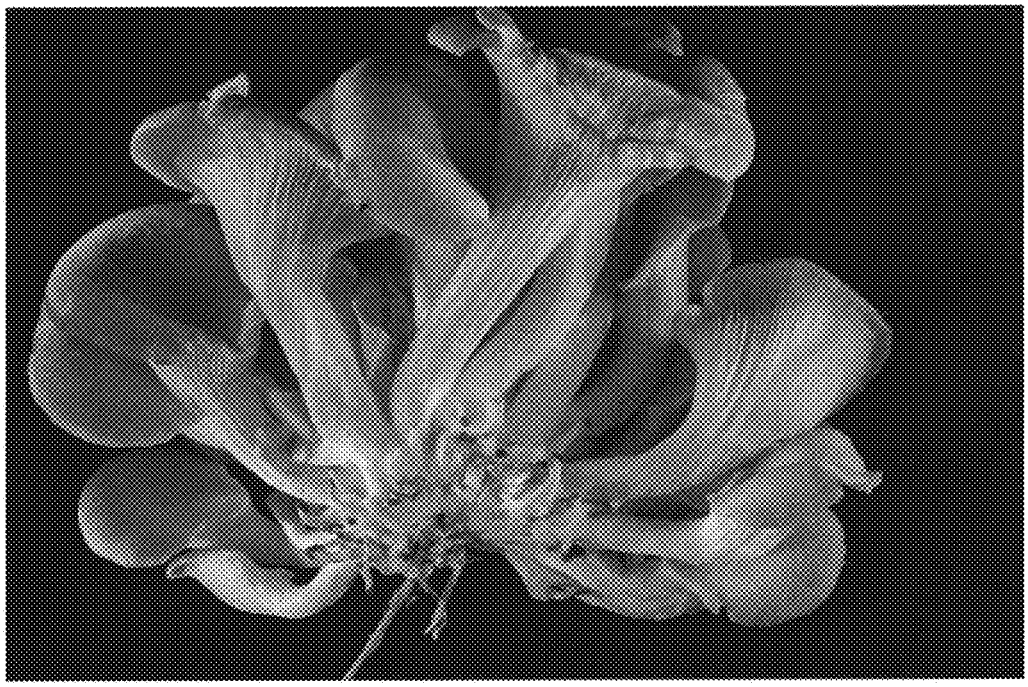
FIG. 1 shows a bundle of 'ALLERPO' mushrooms in their entirety.
Figure 2:
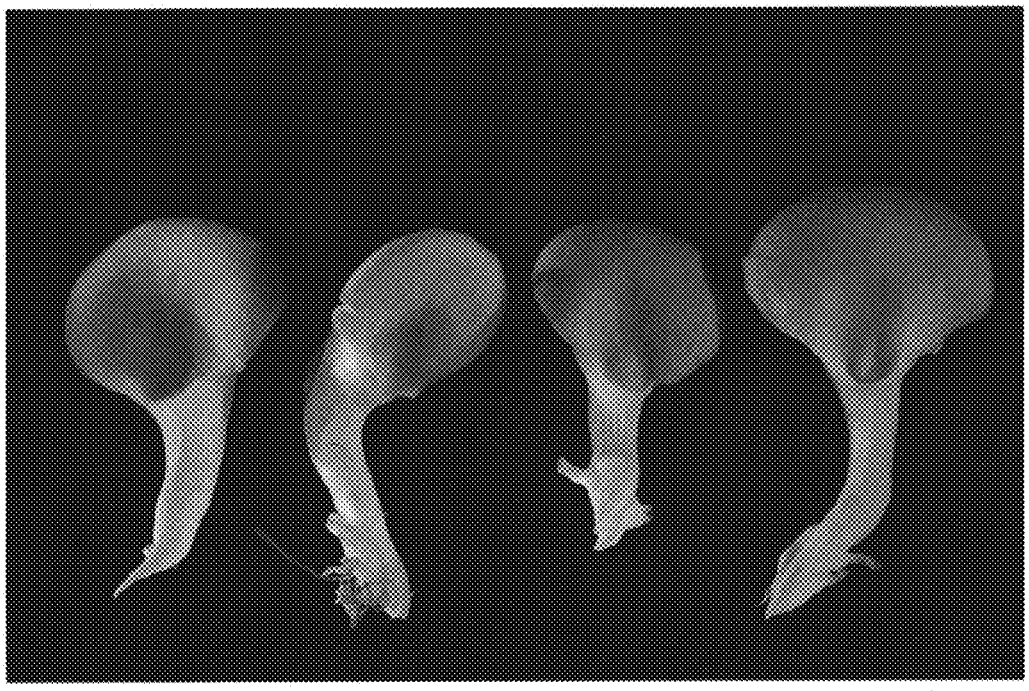
FIG. 2 shows the upper surface of a plurality of 'ALLERPO' mushrooms.
Figure 3:
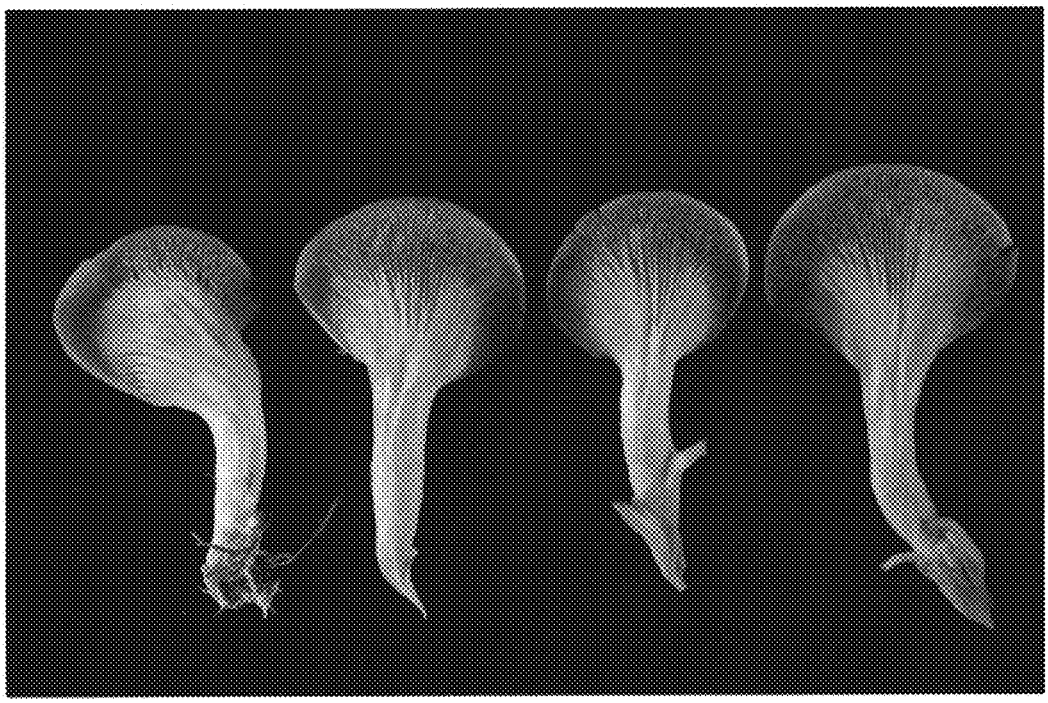
FIG. 3 shows the lower surface of a plurality of 'ALLERPO' mushrooms.
Figure 4:
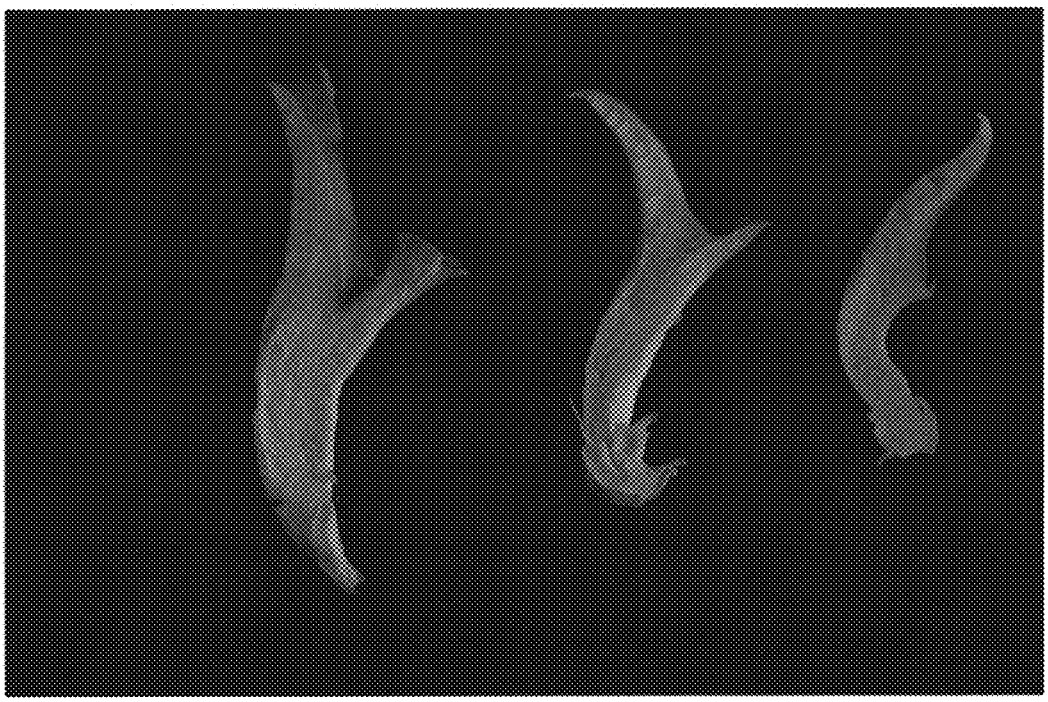
FIG. 4 shows slices of 'ALLERPO' cut transversely.

The following detailed description sets forth the breeding procedures and the characteristics of the new cultivar. In breeding the new variety, parental lines were isolated from HK35 (female parent) (unpatented) and ATCC 58937 (male parent) (unpatented). Strains HK35 and ATCC 58937 were protoplasted to recover their parental genotypes. As they are basidiomycetes, the cells (dikaryons) contain two nuclei, one from each parent of the strain. Protoplasting therefore results in two types of monokaryons (haploids). The parent strains of HK35 were recovered and crosses were made with the parents of ATCC 58937. This created two parallel breeding lines: HK35-parent 1 x ATCC 58937-parent 1 and HK35-parent 2 x ATCC 58937-parent 2. The inability of ATCC 58937 to produce spores is linked to a defect in the msh4 gene. In both breeding lines, molecular markers were used to select offspring containing the defect version of msh4, in combination with as much of the genotype of the HK35 parents. In both breeding lines, a selection of the offspring was used to prepare a backcross with the original HK35 parent. Again, molecular markers were used to select offspring containing the defect version of msh4, in combination with as much of the genotype of the HK35 parents. From each of the parallel breeding lines, a representative haploid strain was chosen. These two strains (each containing a defective msh4 gene) were crossed and this yielded the new variety named 'ALLERPO'.

The new variety is similar in shell-shaped morphology and mushroom yield to HK35, but unlike HK35, 'ALLERPO' does not produce basidiospores. 'ALLERPO' is similar to ATCC 58937 in not producing basidiospores, but differs from ATCC 58937 in morphology and mushroom size (ATCC 58937 produces small, funnel-shaped mushrooms).

'ALLERPO' is very similar to oyster mushroom variety named 'Spoppo' (U.S. Plant Pat. No. 18,037), as they both originate from the same breeding program, using the same parental lines. 'ALLERPO' is similar in morphology to 'Spoppo', however, the cap color of 'ALLERPO' is slightly darker and more brown in color than 'Spoppo'.

Growth Conditions and Reproduction

The oyster mushrooms were grown on fermented wheat straw that is packed into 17-18 kg blocks of about 40×60×20 cm that are wrapped in micro-porous plastic foil. Before packaging, the wheat straw substrate was inoculated with spawn at 25-30 liters per 1000 kg of substrate. During venting, the air temperature is gradually lowered to 14° C., at a relative humidity of 90%.

Botanical Data Collection Conditions and Standards

The color standard used in the present application is the L*a*b* method (also designated as CIE.LAB or CIE-L*a*b*) defined by "Commission International de l'Eclaire" in 1976. The location where measurements were made was Wageningen, The Netherlands. Light conditions where measurements were made were by artificial light provided by a Minolta Chroma Meter type CR-200.

Botanical Description

Number of days from beginning of development to peak development: Based on venting after a 19 day spawn run, first pins appear about 5 days after venting. The first day of harvest is about 10-12 days after venting. A second flush will appear about 25-30 days after venting.

Figure 5:
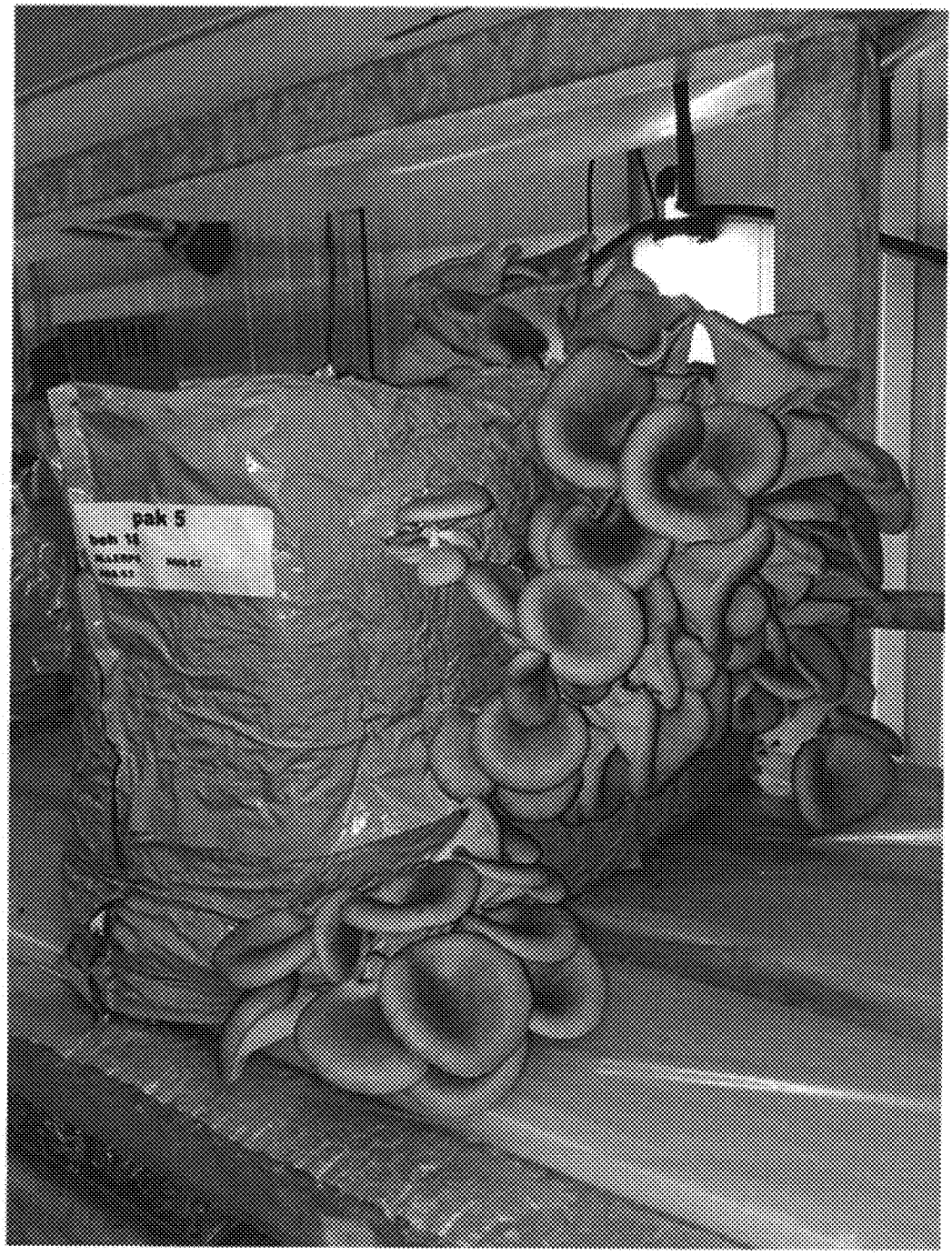
FIG. 5 shows a plurality of 'ALLERPO' mushrooms emerging from their growth medium.

Age of described plant: Oyster mushrooms are generally produced within 5 weeks after inoculation of the straw substrate. The oyster mushrooms are produced as a bundle of mushrooms varying in size. This limits the possibilities for a uniform description of the mushrooms. A bundle of oyster mushrooms of 'ALLERPO' emerging from their growth medium can be seen at FIG. 5.

Overall appearance: Typical of oyster mushrooms, with a brown cap and white, fleshy stipe.

Cap:

*Shape*.—Shell formed, with a stipe that is excentric to the cap center.

*Texture*.—Smooth.

*Pubescence*.—None.

*Margin*.—Smooth.

*Diameter*.—Varies from 4-15 cm.

Figure 6:
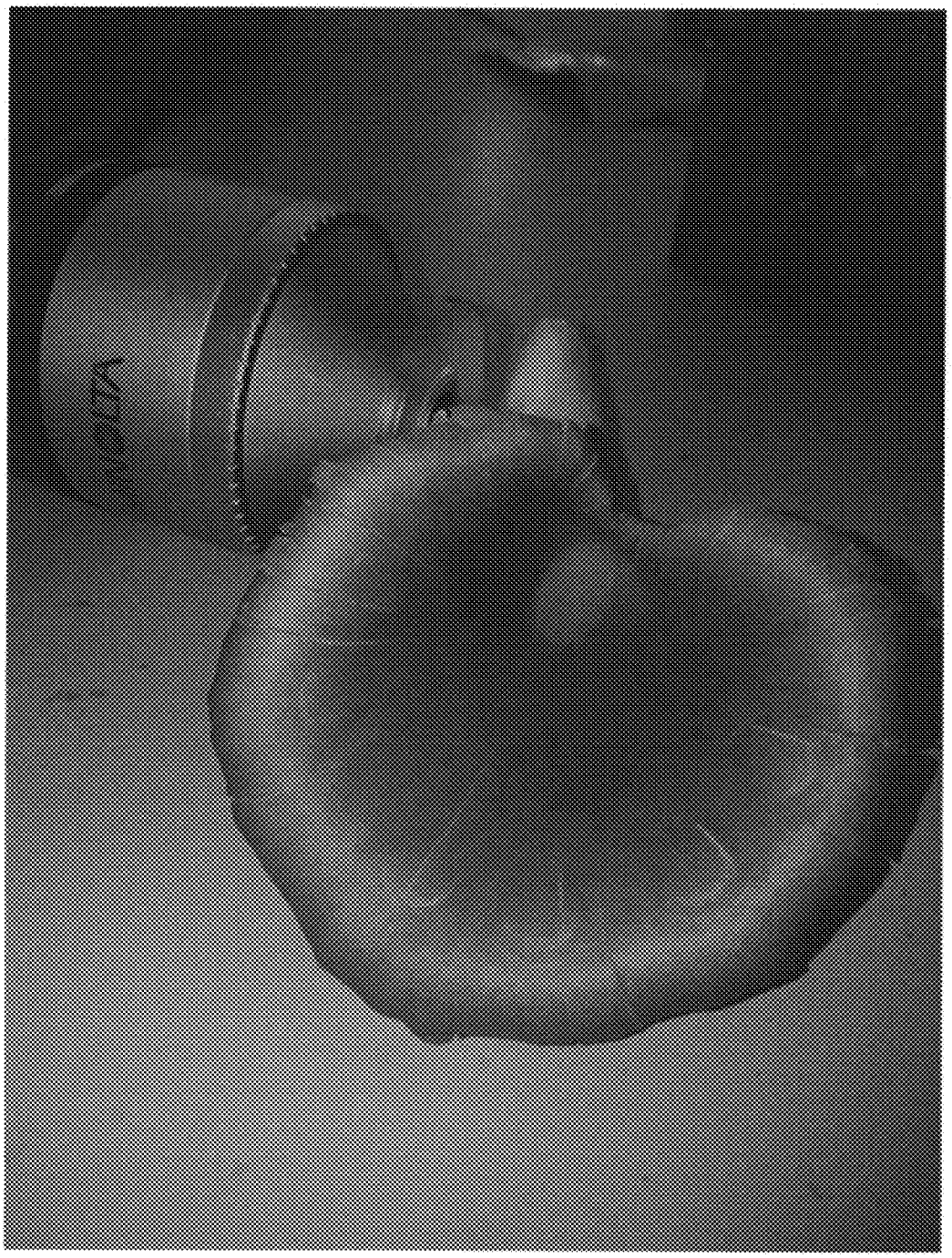
FIG. 6 shows an upper side cap of 'ALLERPO' with lines to designate color measurement location.

*Color*.—L: 67.40 (st. dev. 4.72, n=250), a: 2.207 (st. dev. 0.787, n=250), b: 14.55 (st. dev. 1.80, n=250). The lines of FIG. 6 designate the measured color location approximately halfway between the attachment of the stipe and the edge of the cap.

*Flesh color*.—White, also white upon cutting.

*Flesh/cap thickness*.—Short and variable, as cap size varies considerably between individual mushrooms.

Gills/lamellae:

*Description*.—The lamellae are long and radiate from the stipe outward to the margin of the cap.

*Length*.—46.8 mm (st. dev. 11.2 mm, n=12).

*Width*.—5.6 mm (st. dev. 1.0 mm, n=12).

*Color*.—White.

Stipe/stem:

*Placement*.—Slightly excentric to the middle of the mushroom cap.

*Shape*.—Short and slightly thickened at the base.

*Length*.—51.5 mm (st. dev. 12.6 mm, n=12).

*Width*.—16.8 mm (st. dev. 6.0 mm, n=12).

*Texture*.—Fibrous.

*Pubescence*.—Present at the base.

*Color*.—White.

Spores: None present.

Veil: Not present.

Odor: Typical fungal odor.

General

Disease/pest resistance or tolerance: Nothing unusual noted to date.

Shipping quality: Good.

Temperature tolerance: Between 2 and 32° C.

Market use: For human consumption.

I claim:

1. A new and distinct variety of mushroom plant, as is herein illustrated and described.

* * * * *